United States Patent [19]

Ishak

[11] Patent Number: 5,658,255
[45] Date of Patent: Aug. 19, 1997

[54] NEEDLE APPARATUS

[76] Inventor: Noshi A. Ishak, 87 Spring St., Laconia, N.H. 03246

[21] Appl. No.: 504,565

[22] Filed: Jul. 20, 1995

Related U.S. Application Data

[63] Continuation-in-part of Ser. No. 264,017, Jun. 22, 1994, Pat. No. 5,545,146.

[51] Int. Cl.$^6$ ................................................ A61M 5/32
[52] U.S. Cl. .......................... 604/192; 604/110; 604/263
[58] Field of Search ................................ 604/192, 197, 604/198, 263, 110, 171, 240, 242, 905; 128/919

[56] References Cited

U.S. PATENT DOCUMENTS

| | | | |
|---|---|---|---|
| 4,850,961 | 7/1989 | Wanderer et al. | 604/53 |
| 4,915,697 | 4/1990 | Du Pont | 604/192 |
| 4,923,446 | 5/1990 | Page et al. | 604/198 |
| 4,923,447 | 5/1990 | Morgan | 604/198 |
| 5,011,479 | 4/1991 | Le et al. | 604/198 |
| 5,104,384 | 4/1992 | Parry | 604/192 |
| 5,338,310 | 8/1994 | Lewardowski | 604/192 |
| 5,389,086 | 2/1995 | Attermeier et al. | 604/242 |
| 5,531,706 | 7/1996 | de la Fuente | 604/198 |
| 5,536,257 | 7/1996 | Byrne et al. | 604/198 |

*Primary Examiner*—Michael Powell Buiz
*Assistant Examiner*—V. Alexander
*Attorney, Agent, or Firm*—William B. Ritchie

[57] ABSTRACT

A needle apparatus for intravenous applications which helps prevent needlesticks. The invention includes a needle housing to which a standard hypodermic needle is attached. The needle housing can then be attached to standard syringes via a base. A protective housing surrounds the needle housing which provides two locking positions with the protective housing extended over the needle: the first, is "temporary" which can be removed to restore the needle but still encases the needle, protecting medical personnel from a needlestick; the second is "locked" where the needle cannot be re-exposed, again protecting medical personnel. The protective housing is fitted with a Luer lock so that the apparatus can be used to connect to an I.V. line without requiring the removal of the needle.

7 Claims, 8 Drawing Sheets

NEEDLE APPARATUS

This application is a continuation-in-part of U.S. patent application Ser. No. 08/264,017, filed Jun. 22, 1994, now U.S. Pat. No. 5,545,146.

BACKGROUND OF THE INVENTION

1. Field of the Invention

The invention relates to needles for intravenous applications.

2. Description of the Related Art

Each year, the number of individuals who are infected with Human Immune-deficiency Virus (HIV), Hepatitis B (HPV), and other dangerous diseases is increasing. Currently, the Center for Disease Control (CDC) estimates that from 1.5–2 million people in the United States are infected with HIV. Many of these HIV cases are undiagnosed, which makes anyone who comes in contact with the infected persons body fluids vulnerable to HIV infection as well. Nurses and doctors are particularly vulnerable to HIV infection because their work involves working closely with the body fluids of their patients.

One significant source of HIV exposures for health care workers is accidental needlesticks. The number of accidental needlesticks is estimated to be more than one million per year. Of these, roughly 2% are contaminated by HIV. To make matters worse, about 50% of HIV needlesticks go unreported. The significance of this problem is borne out by the fact that 80% of HIV exposures to health care workers are caused by needlesticks. Of these needlesticks, one in 200 results in an HIV infection. The CDC also estimates that 12,000 health care workers in the United States will become infected with HPV each year. Over 80% of those HPV infections acquired Occupationally by health care workers will be as a result of needlesticks or other sharp instruments. Of those infected, over 200 will die. Clearly, there is a vital need for reducing the occurrence of this type of accident.

Studies reveal that more that 75% of needlesticks occur after use of the needle, in preparation for, or during disposal. Yet despite special precautions such as the use of containers for needles to be discarded and educational programs for health workers, the incidence of needlesticks has not been significantly reduced. Many experts predict that this situation will not change until needles of safer design are introduced.

A common needle design for injections has the needle permanently affixed to the syringe. The disadvantage of this approach is that the syringe does not contain a means of protecting the worker from a needlestick, thus, risking exposure to the health care worker.

Attempts have been made to provide a syringe which allows the needle to be covered by a protective shield. A typical example of this type of apparatus is the B-D Safety -Lok™ syringe marketed by Becton Dickinson and Company. This device has a protective shield that slides over the used needle for preventing contact. However, to protect the needle, such devices, including the B-D Safety -Lok™ design, require that the entire syringe and needle be discarded together. While effective, this approach is more cumbersome because needlesticks are the contributing factor for infection of health care workers, not the syringe itself.

An alternative method to preventing needlesticks is the Needle Pro™ design marketed by Concord/Portex, Smith Industries. This design is covered under U.S. Pat. No. 4,982,842 which discloses a self contained needle with a protective sheath attached. After use of the needle with a syringe, the permanently attached sheath is positioned over the needle so that the needle may be discarded separately from the syringe.

The protective feature of the Needle Pro™ device utilizes a sheath that freely hangs on the side of the needle. However, this sheath can be a distraction when the needle is used in intravenous applications. Also, the device is not adaptable with needleless systems. Furthermore, there is additional dead space by having two needle bases on top of each other. This leads to more waste of the medication and to patients receiving less than the prescribed dosage due to retention of medication by the base surfaces.

As stated earlier, typical needle designs for intravenous applications have the needle affixed to the syringe. If it is desired to use the syringe by connecting it to an I.V. line, the needle must first be removed. Hence, devices that have protective features as part of the syringe will not be utilized, thus presenting the opportunity for an accidental needlestick. With needles that are permanently affixed to the syringe, this means that needle and syringe must both be discarded. When repeated medications are required, a new syringe must be used each time.

A device for injections that provides a needle apparatus that can be mated to needleless syringes and can be connected to an I.V. line without removing the needle and without presenting a danger of needlesticks, even when the needle is removed from the syringe, is not disclosed in the prior art.

SUMMARY OF THE INVENTION

It is an object of the invention to provide a needle apparatus which can be connected to a needleless syringe which can then be used to withdraw medications or give injections.

It is another object of the invention to provide a needle apparatus which completely encloses the needle after use so it cannot produce a needlestick.

It is another object of the invention to provide a needle apparatus which "locks" the needle within the needle apparatus so that it can be connected to an I.V. line without removing the needle or be safely discarded if already used.

It is another object of the invention to provide a needle apparatus which "temporary locks" the needle within the needle apparatus after medication has been withdrawn but can re-expose the needle for injecting the medication into the patient or I.V. line.

It is another object of the invention to provide a needle apparatus which utilizes a color coding scheme to allow easy visual verification on the positioning of needle apparatus in the "locking" or "temporary locking" position.

It is a final object of the invention to provide a needle apparatus which can be used to connect to needleless ports of I.V. lines to administer medications without requiring the removal of the needle.

The invention is a needle apparatus for injection and intravenous medical procedures. A needle is provided that is adapted to inject or withdraw fluids. A needle housing is provided that has a base that is attachable to a standard syringe. Said needle housing has an elongated nose section that permanently holds said needle. Said nose section has an exterior cross-sectional profile and has a tip. A protective housing is provided that has a needle opening corresponding to said needle. Said protective housing also has a recess, said recess having an interior cross-sectional profile corresponding to said exterior cross-sectional profile of said nose section. Locking means, associated with said protective housing and said needle housing, are provided for holding said protective housing in a "fixed extended position" relative to said needle housing such that when said protective housing is in the "fixed extended position", the point of said needle is held within the interior walls of said outer housing. Temporary locking means, associated with said protective housing and said needle housing, are also provided for holding said protective housing in a "temporary extended position" relative to said needle housing such that when said protective housing is in the "temporary extended position", the point of said needle can be re-exposed. The nose of said needle housing has color bands to allow easy visual verification of the position of said needle protective housing in either the "temporary extended position" or the "fixed extended position". Connection means, attached to said protective housing, are provided for connecting said apparatus to an I.V. line when said protective housing is in the fixed extended position, without removing said needle from said apparatus.

DETAILED DESCRIPTION OF THE INVENTION

Figure 1:
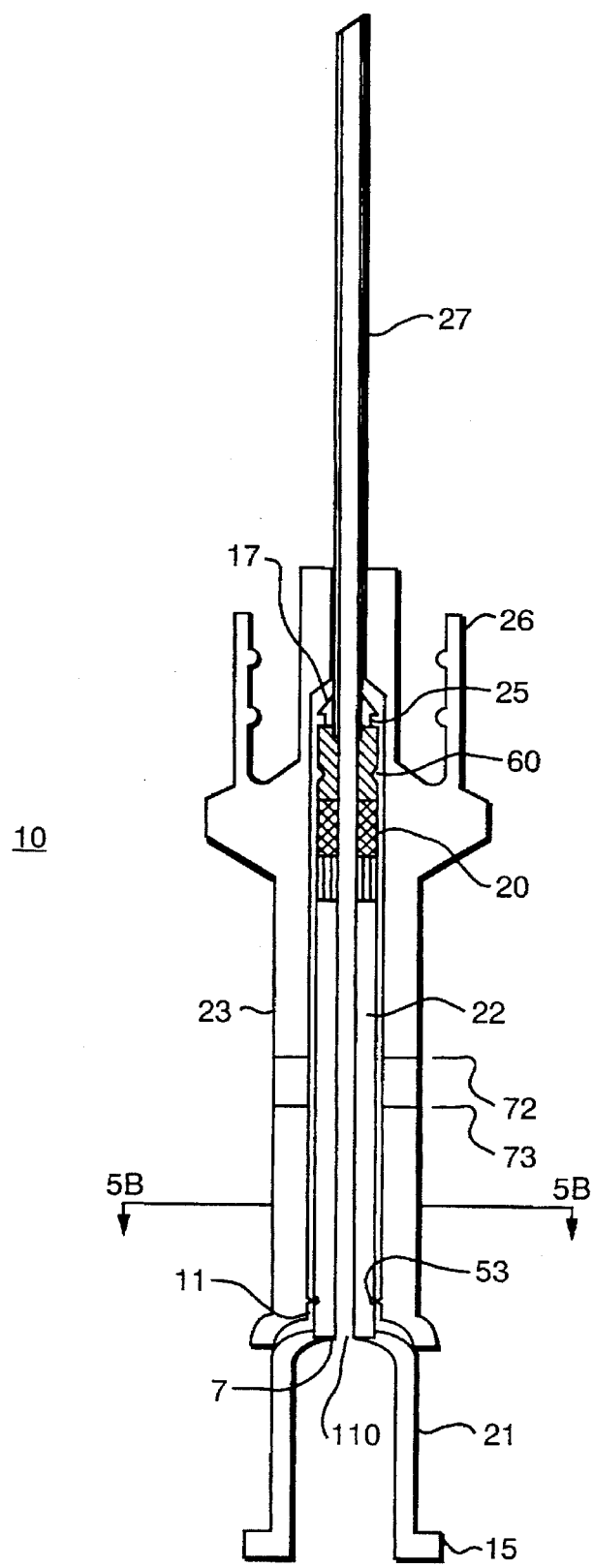
FIG. 1. is a longitudinal cut-away view of the needle apparatus, showing the needle before use in accordance with the invention.
Figure 2:
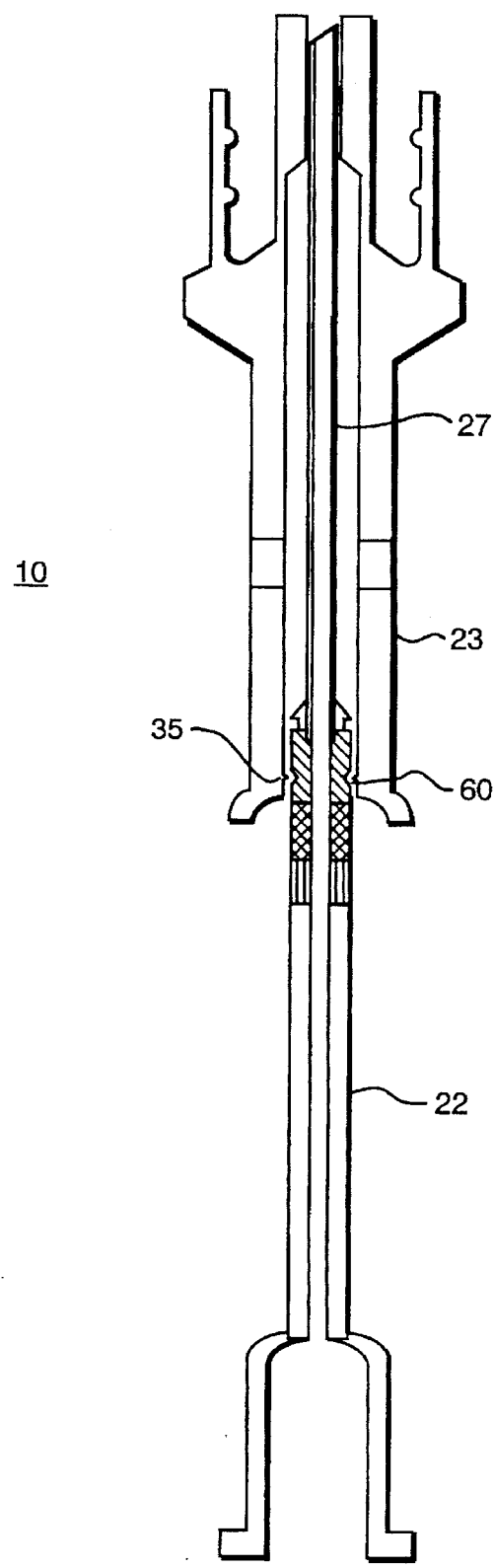
FIG. 2 is a longitudinal cut-away view of the needle apparatus, showing the protective guard housing partially advanced in the "temporary extended position" to protect the needle.
Figure 3:
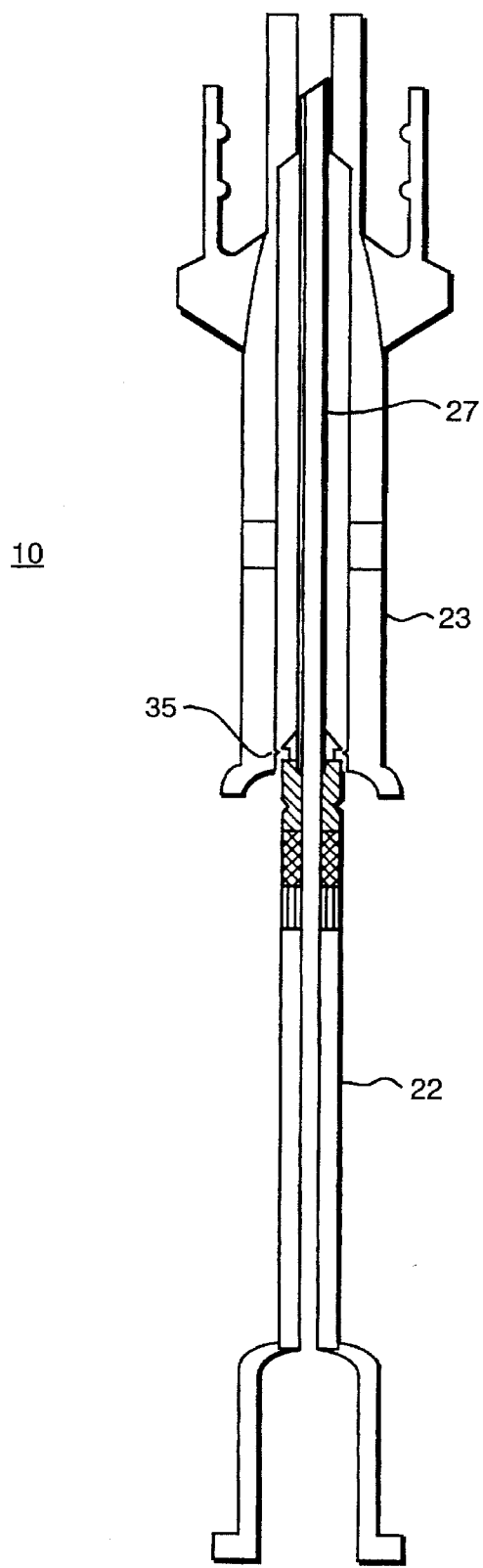
FIG. 3 is a longitudinal cut-away view of the needle apparatus, showing the protective guard housing fully advanced in the "fixed extended position" to protect the needle.

Referring now to FIGS. 1–3, needle apparatus 10 with needle 27 is shown in the ready-to-use, unprotected position; with the guard housing partially extended to protect the needle; and with the guard housing fully extended, in the locked position. In the locked position, needle apparatus 10 can be connected to an I.V. line (not shown) via Luer lock 26 without removing the needle or can be safely discarded if already used. The materials selected for the construction of the invention are preferably plastics, well known in the art for constructing such medical devices.

Figure 5A:
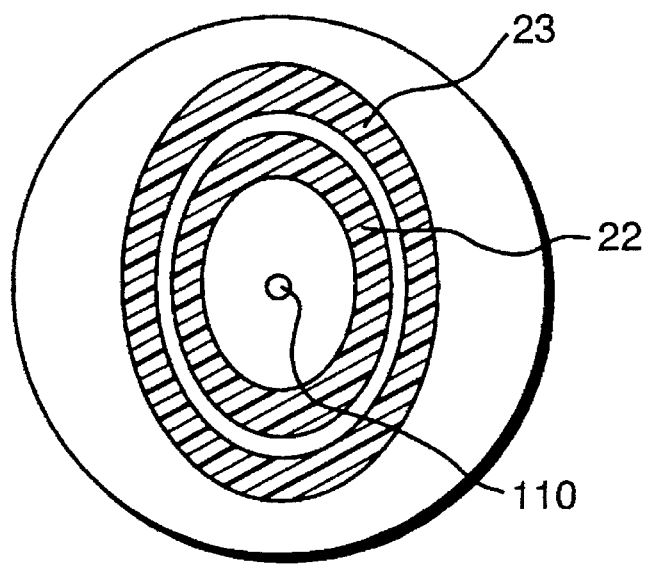
FIG. 5A is a cross-sectional view of the needle protective guard over the needle base along section lines AA as shown in FIG. 1.
Figure 5B:
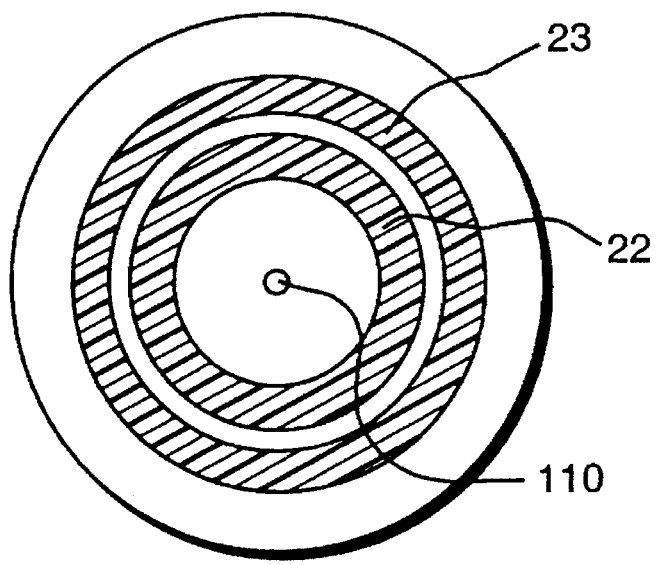
FIG. 5B is a cross-sectional view of an alternate embodiment of the needle protective guard over the needle base along section lines AA as shown in FIG. 1.

The external shape of the invention, including housings 22 and 23, are preferably oval but other cross-sectional shapes would be acceptable. FIG. 5A is a cross-sectional view of protective housing 23 over needle housing 22. The oval cross-section allows for a firmer grip because it prevents rotation of protective housing 23 over needle housing 22. FIG. 5B is an alternative embodiment of invention 10 using a circular cross-section. Manufacture can be performed in a number of ways, however, the most practical from a cost and quantity perspective is injection molding.

Referring again to FIGS. 1–3, needle 27 is rigidly attached to needle housing 22. Needle 27 is preferably constructed of medical grade stainless or other materials that have been approved for needle use. Needle 27 is attached using techniques well known in the art, such as electrowelding. By extending the length of needle 27, insertion into needle housing 22 can extend all the way through to point 7 if so desired. At the "syringe" end of needle housing 22, needle housing 22 is flared to provide attachment base 21. Flange 15 is provided at the end of attachment base 21 and serves to releasably attach invention 10 to a standard hypodermic syringe (not shown). Nose 20 of needle housing 22 is preferably about 1 inch long and is sized according to the length of protection housing 23 which is mated to nose 20. In turn, protective housing 23 must be sufficiently long to completely enclose needle 27 when the device is in a protective position as shown in FIGS. 2 and 3. Consequently, to accommodate different lengths of needles, the lengths of protective housing 23 and needle housing 22 may have to be adjusted accordingly.

When invention 10 is attached to a standard syringe, invention 10 and the attached syringe can be used to withdraw medication fluids or administer injections via needle 27.

FIG. 2 is a longitudinal cut-away view of needle apparatus 10, showing protective guard housing 23 partially advanced in the "temporary extended position" to protect needle 27. Protective housing 23 is positioned in temporary locking groove 60. Temporary locking groove 60 is symmetrical around nose 20. If the needle is not yet ready to be discarded but in need of protection, protective housing 23 is advanced until locking ridge 35 is engaged with temporary locking groove 60. Either one "click" sound or by feel of the restraint placed upon protective housing 23 will provide medical personnel feedback that needle apparatus 10 is in the temporary locking position. A useful application of this feature is to protect needle 27 after medication has been withdrawn while allowing needle 27 to be re-exposed to inject medication into a patient or to be used with an I.V. line.

Needle 27 can be protected in two different positions. One is with protective housing 23 being retained by temporary locking groove 60, as discussed in the previous paragraph. The other position is when protective housing 23 is fully extended in the locked position. FIG. 3 is a longitudinal cut-away view of needle apparatus 10, showing protective housing 23 fully advanced in the "fixed extended position" to protect needle 27.

Figure 4:
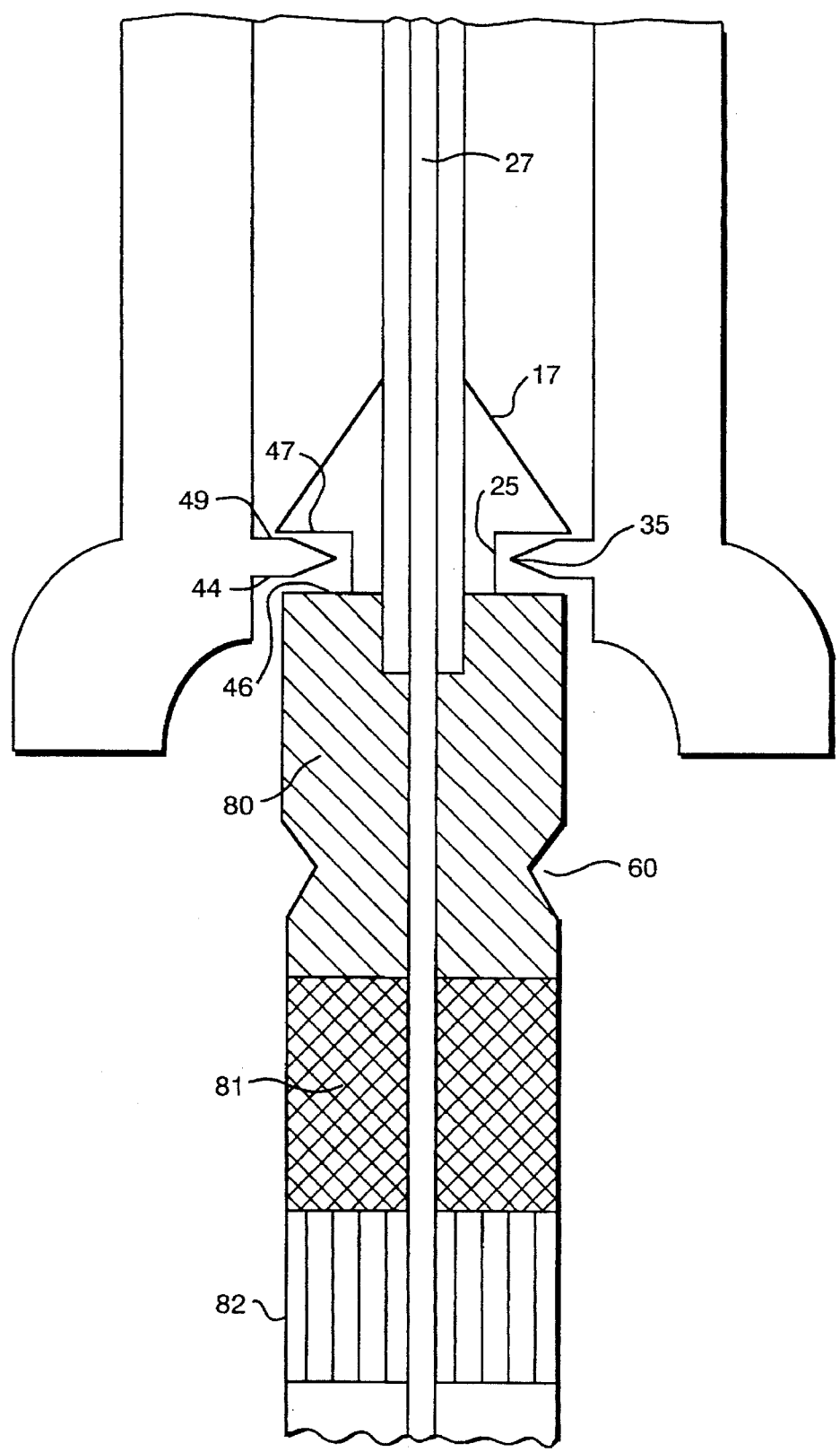
FIG. 4 is a detailed longitudinal cut-away view of the locking mechanism that holds the apparatus in the protected position.

To provide a means for visual verification on the positioning of protective housing 23, nose 20 has three color bands, as shown in FIG. 4. The color bands are red 82, orange 81 and green 80. The method for colorized plastic is well known in the art. Size of the color bands are selected such that when protective housing 23 is in the temporary locking position, only red 82 and orange 81 color bands are visible. For the locked position of protective housing 23, the green 80 color band is also visible with the red 82 and orange 81 color bands.

Locking groove 25 is symmetrical around tapered tip 17 of needle housing 22. Tapered tip 17 allows easier assembly of protective housing 23 over needle 27 and needle housing 22. Locking groove 25 is circumferentially notched so protective housing 23 can be held in position. As shown in FIG. 3, once needle 27 has been used and protective housing 23 is fully extended, needle 27 is entirely enclosed within protective housing 23, thereby preventing a user from being injured by needle 27.

As shown in FIG. 4, locking groove 25 is preferably shaped with vertical ridges, as indicated by surfaces 46 and 47. In order to permit installation of protective housing 23 past locking groove 25, protective housing 23 is heated to a sufficient temperature during the assembly process so that the elastic properties of the plastic allow enough of a gap for installation of protective housing 23 past locking groove 25. An alternative method of installation would require protective housing 23 to consist of two halves that are welded or sealed together after they are positioned in place. Both installation methods are well known in the art.

After needle 27 has been used and protective housing 23 has been fully extended, surface 46 on needle housing 22 butts up against surface 44 on protective housing 23 to stop needle housing 22 from being moved past locking groove 25. At this point, slidable outer protective housing 23 is permanently locked in place and needle 27 becomes enclosed with no exposed sharp points, ready for disposal housing. To prevent protective housing 23 from being pulled off needle housing 22 once needle housing 22 is inserted into protective housing 23, surface 47 on needle housing 22 butts up against surface 49 on protective housing 23 to stop needle housing 22 from being removed past locking groove 25.

Figure 4A:
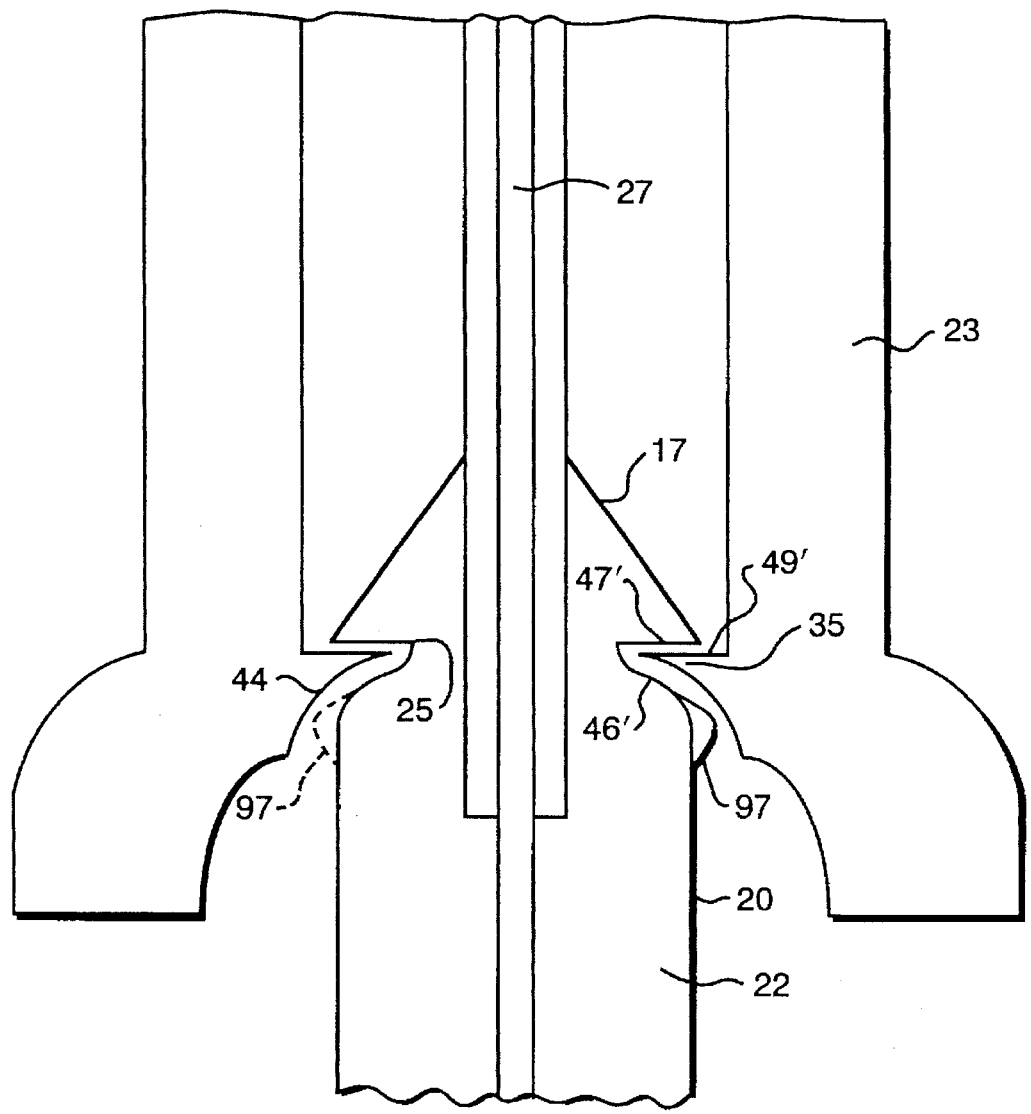
FIG. 4A is a detailed longitudinal cut-away view of an alternative embodiment of the locking mechanism shown in FIG. 4.

As an alternative embodiment, as shown in FIG. 4A, locking groove 25 is shaped with an upwardly sloped ramp surface on surface 46'. This facilitates needle housing 22 sliding over locking ridge 35 which has a similarly sloped ramp 44. To prevent protective housing 23 from being removed from needle housing 22 once needle housing 22 is inserted into protective housing 23, surface 47' on needle housing 22 and surface 49' on protective housing 23 stop needle housing 22 from being removed past locking groove 25. Further security to prevent needle housing 22 from being retracted can be provided by optional ridge 97, shown in dotted lines.

Figure 4B:
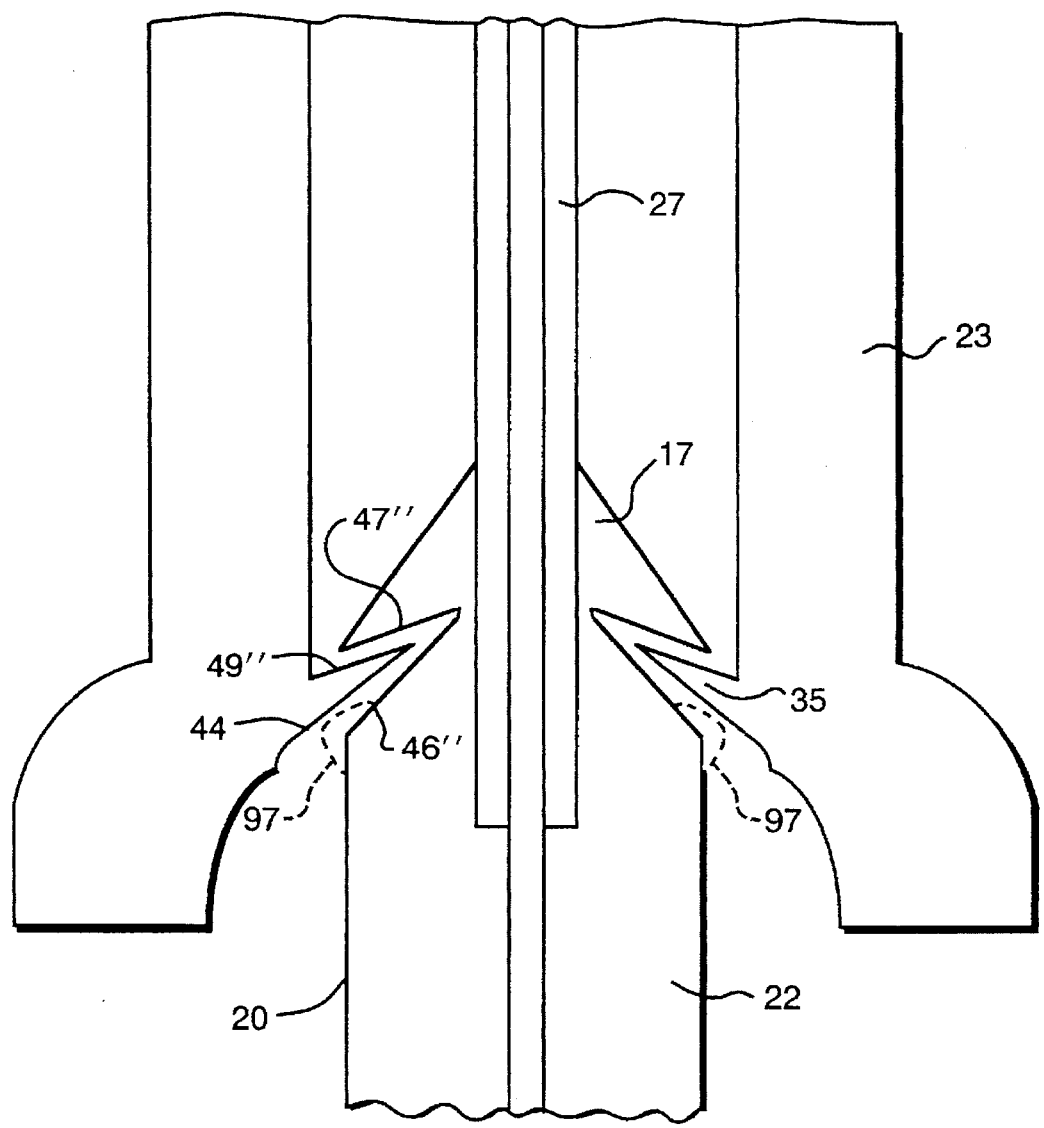
FIG. 4B is a detailed longitudinal cut-away view of another alternative embodiment of the locking mechanism shown in FIG. 4.

As another alternative embodiment, as shown in FIG. 4B, surfaces 47" and 49" may also be made with upwardly sloping ramps which will provide a more positive locking position once protective housing 23 is slid into the "needle protected" position. As above, to provide additional security to prevent needle housing 22 being retracted, optional ridge 97, shown by dotted lines, can be utilized.

To retain protective housing 23 in place and prevent it from sliding on needle housing 22 while needle 27 is exposed, needle housing 22 may be fitted with ridge 53 which will keep the respective housings in position in the "needle use" mode. Ridge 53 is preferably a small rounded section that is molded into needle base 22. Ridge 53 does not "lock" protective housing 23 in position, but merely serves as a temporary point of stability.

To facilitate sliding protective housing 23 into position, knurled surfaces 72 and 73 can also be molded into protective housing 23. Surfaces 72 and 73 will enable a user to have a more firm grip on protective housing 23 in order to slide it more securely.

Protective housing 23 is of substantially hollow construction and is fitted with recess 11 which corresponds to the cross-sectional profile of nose 20 of needle housing 22. Needle housing 22 is also of substantially hollow construction and is fitted with recess 110 which corresponds to the cross-sectional profile of needle 27.

As shown in FIG. 3, once protective housing 23 is fully extended and locked via locking ridge 35 and groove 25, needle 27, including the tip of needle 27, is completely enclosed. When protective housing 23 is full retracted, locking ridge 35 rests on attachment base 21 as shown in FIG. 1. Once locked in place, the length of protective housing 23 must extend past the tip of needle 27, as shown in FIGS. 2 and 3 in order to provide protection from needlesticks. Protective housing 23 is supplied with Luer lock 26, as shown in FIGS. 1, 2 and 3. Luer lock 26 allows the needle apparatus to be connected or secured to an I.V. line without removing the needle. This saves a substantial amount of time, avoids wasting syringes and prevents needlesticks.

Figure 6:
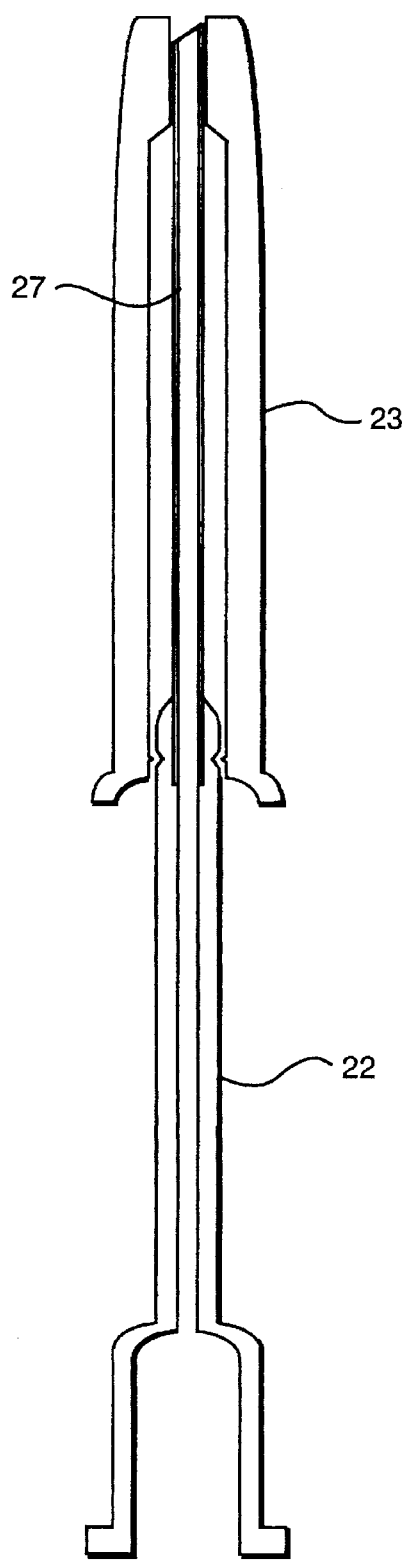
FIG. 6 is a longitudinal cut-away view of an alternative embodiment of the invention.

FIG. 6 is a view of an alternative embodiment of invention 10. In this embodiment, protective housing 23 is designed as a standard syringe tip without Luer lock 26. As in the preferred embodiment, the operator is prevented from a needlestick since needle 27 is completely enclosed by protective housing 23 when protective housing 23 is locked into place on needle housing 22.

To use needle apparatus 10, a syringe (not shown) is first inserted into attachment base 21. Outer protective housing 23 is in a retracted position, thus exposing needle 27 as shown in FIG. 1. The operator is ready to use needle 27 to withdraw medications or give injections. Once needle 27 has been used, the operator grabs attachment base 21 with one hand and protective housing 23, preferably at knurled surfaces 72 and 73, with the other hand and fully extends protective housing 23 to enclose needle 27. Protective housing 23 is pushed toward needle 27 tip until locking ridge 35 snaps into place with temporary locking groove 60. Protective housing 23 can continue to be pushed toward needle 27 tip until locking ridge 35 snaps into place with locking groove 25. At this point, slidable outer protective housing 23 is securely locked in place as indicated by all three color bands showing and needle 27 becomes totally enclosed with no exposed sharp points, ready for disposal.

As an alternative use of needle apparatus 10, connection can be made to needleless ports of I.V. lines to administer medications without the need to remove needle 27. A syringe is merely inserted into attachment base 21 when medication is needed to be administered. Once needle 27 is removed, it can be completely enclosed and securely locked within protective housing 23 for disposal.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

What is claimed is:

1. A needle apparatus for intravenous medical procedures comprising:
   a needle adapted to inject or withdraw fluids;
   a needle housing with a base that is attachable to a standard syringe, said needle housing having an elongated nose section that permanently holds said needle, said nose section having an exterior cross-sectional profile and having a tip;
   a protective housing having a needle opening corresponding to said needle, and a recess, said recess having an interior cross-sectional profile corresponding to said exterior cross-sectional profile of said nose section, such that when said protective housing is at least partially retracted, the tip of said needle is unprotected;

locking means, associated with said protective housing and said needle housing, for holding said protective housing in an extended position relative to said needle housing such that when said protective housing is in said extended position, the point of said needle is held within the interior walls of said outer housing, said locking means further comprising:

a locking ridge protruding circumferentially from said recess of said protective housing and a locking groove circumferentially adjacent to said tip of said nose section of said needle housing such that when locking ridge engages said locking groove, said protective housing cannot be removed from said needle housing, such that when said protective housing is so disposed relative to said protective housing, said extended position is locked; and a temporary locking ridge protruding circumferentially from said recess of said protective housing and a locking groove circumferentially adjacent to said tip of said nose section of said needle housing such that when temporary locking ridge engages said locking groove, said protective housing can be pulled back to re-expose said needle, such that when said protective housing is so disposed relative to said protective housing, said extended position is releasable.

2. The apparatus of claim 1 wherein said needle housing further comprises color bands to allow easy visual verification of the position status of said protective housing relative to said needle housing.

3. The apparatus of claim 2 where the color red on said needle housing is used to indicate at least a partially retracted position; the color orange is used to indicate the extended position that is releasable; and the color green is used to indicate the extended position that is locked.

4. The apparatus of claim 3 further comprising:

connection means, attached to said protective housing, for connecting said apparatus to an I.V. line when said protective housing is in the extended position, without removing said needle from said apparatus.

5. The apparatus of claim 4 wherein said protective housing further comprises at least one textured surface such that a user can more easily slide said protective housing to the fixed extended position.

6. The apparatus of claim 5 further comprising retaining means for releasably holding said protective housing in a fully retracted position relative to said needle housing such that when said protective housing is in the fully retracted position, said needle is outside of said protective housing, ready for use to inject or withdraw fluids.

7. The apparatus of claim 6 wherein said retaining means further comprises a retaining ridge protruding circumferentially from said recess of said protective housing adjacent to said needle opening such that when said protective housing is in the fully retracted position, said retaining ridge releasably engages said locking groove, thereby releasably holding said protective housing in the fully retracted position.

* * * * *